United States Patent [19]

Brot et al.

[11] 4,374,928

[45] Feb. 22, 1983

[54] NOVEL REDUCTASE

[75] Inventors: Nathan Brot, West Orange; Herbert Weissbach, Cedar Grove, both of N.J.

[73] Assignee: Hoffmann-La Roche Inc., Nutley, N.J.

[21] Appl. No.: 269,150

[22] Filed: Jun. 1, 1981

[51] Int. Cl.$^3$ .................. C12P 21/00; C12N 9/02; C12Q 1/26; A61K 37/50

[52] U.S. Cl. ................................ 435/68; 435/189; 435/25; 424/94

[58] Field of Search .............................. 435/68, 189

[56] References Cited

PUBLICATIONS

Ejiri et al., Analytical Biochemistry, vol. 102, pp. 393-398, (1980).
Ejiri et al., Journal of Bacteriology, vol. 139, No. 1, pp. 161-164, (1979).
Wong et al., Biochemical and Biophysical Research Communications, vol. 96, No. 3, pp. 1449-1454, (1980).
Black et al., J. Biol. Chem. 235, 2910-2916, (1960).

*Primary Examiner*—Lionel M. Shapiro
*Attorney, Agent, or Firm*—Jon S. Saxe; George M. Gould; John B. Wilson

[57] ABSTRACT

A novel reductase which is an enzyme that can catalyze the reduction of methionine sulfoxide resides in proteins is described. The enzyme has been found in *E. coli, Euglena gracilis, Tetrahymena pyriformis,* Hela cells, rat tissue and spinach. The enzyme has an estimated molecular weight of about 18,000-20,000. It can be used to restore biological activity to proteins inactivated by oxidation of methionine residues.

7 Claims, No Drawings

NOVEL REDUCTASE

BACKGROUND OF THE INVENTION

Lampen et al., Arch. Biochem. Biophys. 13, 33 (1947) and Sourkes and Trano Arch. Biochem. Biophys. 42, 321 (1953) reported in vivo experiments that suggested the presence of an enzyme system in *E. coli* that converts free methionine sulfoxide (MetSO) to methionine. These reports were confirmed by Ejiri et al. in two recent publications, J. Bact. 139, 161 (1979) and Anal. Biochem. 102, 393 (1980).

A similar reaction was first described in yeast by Black et al. J. Biol. Chem. 235,2910 (1960) who showed that three protein factors were required. These protein factors were later shown to be thioredoxin, thioredoxin reductase and the enzyme directly responsible for the reduction of MetSO. A MetSO reducing system has also been found to be present in animal tissues and plants.

There are a number of proteins whose biological activity is destroyed upon oxidation of methionine residues to MetSO and it is known that a wide variety of oxidizing agents produced in tissues can oxidize protein bound methionine. Although the deleterious effect of those oxidizing agents would be expected to be neutralized by various cellular enzymes (e.g. catalase, peroxidase, superoxide, dismutase), it is apparent that the efficiency of these systems is not sufficient to preclude some oxidation of methionine residues in proteins. For proteins with slow turnover, this oxidation could be crucial if methionine residues are involved in the function of the protein.

It is known, for example, that alpha-1-proteinase inhibitor ($\alpha$-1-PI), which is a major serine endopeptidase inhibitor in plasma, is inactivated when exposed to oxidizing agents which cause the oxidation of specific methionine residues to MetSO. Furthermore it has been found that $\alpha$-1-PI isolated from human rheumatoid synovial fluid is inactive and contains MetSO residues near its reactive center [Pong and Travis, Biochem. Biophys. Res. Comm. 96, 1449–1454 (1980)]. The inactivation of $\alpha$-1-PI, as by oxidants in cigarette smoke [Science 206, 1315–1316 (1979)], results in an increased elastase activity which is responsible for the loss of lung function in emphysema. It is also known for instance that the difference between normal and cataractous lens proteins in the high level of MetSO residues in the cataractous lens protein.

SUMMARY OF THE INVENTION

The present invention relates to a reductase endogenous to biological cells, purified to be essentially free of other endogenous peptides and being able to reduce MetSO residues in proteins or peptides to methionine. This reductase does not reduce MetSO to methionine where the MetSO is not contained in a peptide or protein. This reductase is useful in restoring or maintaining the biological activity of proteins which otherwise would be inactivated by oxidation of essential methionine residues to MetSO. The reductase of this invention is useful for example more particularly in reversing the inactivation of $\alpha$-1-PI, which inactivation has been caused by the oxidation of methionine residues in $\alpha$-1-PI to MetSO, especially in cases where the modulation of elastase in lung is desired as in instances of increased elastase activity in emphysema patients and cigarette smokers.

DETAILED DESCRIPTION OF THE INVENTION

The present invention relates to the isolation, purification and characterization of a novel reductase endogenous to biological cells. The reductase of this invention is an enzyme that reduces MetSO residues to methionine in proteins or peptides containing methionine oxidized to MetSO. The reductase of this invention (hereafter referred to as peptide MetSO reductase) is unique in that it reduces peptide or protein bound MetSO and does not reduce free MetSO, and has been obtained essentially free of other biologically endogenous proteinacious substances.

Peptide MetSO reductase may be prepared from any biological cells capable of reducing MetSO residues of proteins to methionine residues. Among these bilogical cells are included cells such as those from *E. coli, Euglena gracilis, Tetrahymena pyriformis,* spinach, Hela, and animal tissue such as liver, kidney, heart, lung and brain as from the rat. A preferred source of peptide MetSO reductase is *E. coli.*

In a typical preparation procedure peptide MetSO reductase is obtained from *E. coli* cultured and harvested by conventional processes. Cell free extracts from *E. coli* are obtained by methods well known in the art and the peptide MetSO reductase therein purified to be essentially free of other proteinacious substances by conventional chromatographic methods and salt fractionations, i.e. gel filtration as by DEAE-Sephadex, Ultrogel AcA-44 and DEAE-cellulose column chromatographies and salt precipitations as with $(NH_4)_2SO_4$. The purification and preparator procedure for peptide MetSO reductase may be followed by any suitable assay of the enzymatic activity of peptide MetSO reductase, i.e. an assay following the conversion of MetSO residues in protein to methionine or following the restoration of biological activity to a protein that has lost activity due to the oxidation of methionine residues.

It has been found, for example, that a suitable assay for detecting a peptide MetSO reductase system is one employing *E. coli* ribosomal protein L12 (designated hereafter Met-L12). Previous studies with *E. coli* Met-L12 has shown that chemical oxidation of the methionine residues in Met-L12 to MetSO (providing thereby MetSO-L12) resulted in the loss of biological activity. It has also been shown that MetSO-L12 could no longer bind to 50S ribosomal subunits depeleted of L12, interact with another protein designated L10 to form an L12·L10 complex, or be acetylated on the amino terminal serine to form a protein designated L7. This last reaction surprisingly provided a simple assay to measure the conversion of MetSO-L12 to Met-L12.

That is, peptide MetSO reductase catalyzes the reduction of methionine sulfoxide residues in MetSO-L12 to methionine residues providing thereby Met-L12 which could then be enzymatically acetylated by conventional use of L12 transacetylase to provide acetyl-Met-L12, and the amount of acetyl-Met-L12 determined in a conventional manner. With the purified peptide MetSO reductase, this assay reaction is proportional to protein concentration above 1 $\mu$g. per incubation and is linear with time over a 60 minute period of incubation. Where MetSO-L12 is used as substrate for peptide MetSO reductase, the Met-L12 formed could by enzymatically acetylated and the amount of acetyl-Met-L12 determined. Ideally, the enzyme activity of peptide MetSO reductase should be reported in terms of MetSO residues in MetSO-L12 that are reduced. Such a value can be determined if one takes into account the fact that the L12 transactylase used in the assay for acetylation only acetylates about ⅓ of its substrate (Met-L12) and if the assumption is made that all 3 methionine residues in MetSO-L12 must be reduced to restore biological activity. Since it was found that an average of 16 pmol of acetyl-Met-L12 was formed per µg of peptide MetSO reductase employed, this would represent the reduction of 144 pmoles of MetSO in MetSO-L12 as determined by conventional calculations.

The effect of peptide MetSO reductase as an effective agent for reducing MetSO residues in any proteins or peptides to corresponding methionine residues can be carried out and/or determined by any established art recognized methods which would permit the peptide MetSO reductase to react with a MetSO containing protein or peptide. Proteins or peptides which may act as a substrate for peptide MetSO reductase are any proteins or peptides of synthetic or biological origin, which proteins or peptides contain one or more MetSO residue therein. Examples of such proteins which may contain MetSO and thereby act as substrate for peptide MetSO reductase are, for example, MetSO-L12, MetSO-enkephalins, and alpha-1-proteinase inhibitor having a MetSO residue.

Peptide MetSO reductase obtained from a homologous source may be administered to warm blooded mammals. The administration may be by any conventional technology such as by conventional mist forming means as by an aerosol spray or by parenteral application either intravenously, subcutaneously or intramuscularly. Obviously the required dosage will vary with the particular condition being treated, the severity of the condition, the duration of the treatment and the means employed for administration. A suitable dosage form for pharmaceutical use may be obtained from lyophilized peptide MetSO reductase reconstituted prior to use in a conventional manner.

By conventional chromatography on Ultrogel, the molecular weight of peptide MetSO reductase is approximately 18,000-20,000.

The enzymatic activity of peptide MetSO reductase is not significantly inhibited by large excess of free MetSO. In fact in an assay for reducing MetSO residues in a peptide substrate, free MetSO at a concentration of $1 \times 10^{-4}$ M (which was about 60 times the concentration of substrate) caused less than a 20% inhibition of the enzymatic activity of peptide MetSO reductase in the assay.

Furthermore, Peptide MetSO reductase obtained in accordance with this invention is essentially free of transacetylase activity.

The present invention is further illustrated by the following examples.

EXAMPLE 1

Ribosomal protein L12 was isolated and purified from *E. coli* ribosomes as described by Brot et al., J. Biol. Chem. 248, 6952 (1973). The methionine residues in L12 were oxidized with N-chlorosuccinamide using the procedure of Schechter et al. Biochemistry 14, 4497 (1975). The oxidized L12 was dialyzed for 16 h against a buffer containing 10 mM each of Tris-Cl, pH 7.9, $MgCL_2$ and $NH_4Cl$ (buffer A). Oxidized Met-enkephalin (MetSO-enkaphalin) was obtained by conventional procedures. The methionine residue in [tyrosyl-3,5-$^3$H] enkephalin (5-L-methionine) was oxidized to methionine sulfoxide by incubating the enkephalin in a mixture containing 50 µl dimethylsulfoxide, 250 µl 12N HCl and 500 µl glacial acetic acid in a final volume of 1 ml. After 15 min at 23° the reaction mixture was dried by evaporation under vacuum and dissolved in 740 µl of 4 M urea containing 1 M formic acid and 0.8 M pyridine. The oxidized Met-enkephalin was purified by high performance liquid chromatography (HPLC) on an RP-8 column as described by Lewis et al., Int. J. Peptide Protein Res. 13, 493 (1979).

EXAMPLE 2

Assay for peptide MetSO-reductase

The assay for the reduction of MetSO-L12 to L12 is based on the ability of L12-transacetylase to specifically acetylate the amino terminal serine of Met-L12 to form acetyl-Met-L12, i.e. L7. A two-step incubation was used. The first reaction (i.e. reduction) contained in a total volume of 15 µl; 33 mM Tris-Cl, pH 7.4, 13 mM $MgCL_2$, 275 pmol MetSO-L12, 13 mM dithiothreitol (DTT), and enzyme (see below). After a 60 min incubation at 37°, the reaction mixtures were placed on ice and to each reaction mixture were added 2 µmol of sodium arsenite, 1.2 µg partially purified L12-transacetylase (see below) and [$^3$H] acetyl-CoA (935 pmoles, 237 cpm/pmol) and the volume brought to 50 µl. The second incubation (acetylation reaction) was for 5 min at 37°, after which the reaction mixtures were diluted with 3 ml of cold buffer A and filtered through a nitrocellulose filter. The filters were washed with 10 ml of this same buffer, dissolved in scintillation fluid and the radioactivity determined. Under these conditions L12 and acetyl-L12 are quantitatively retained by the nitrocellulose filter. The results are reported as pmoles of acetyl-L12 formed under these conditions.

EXAMPLE 3

Assay for MetSO reductase

The assay for the conversion of methionine sulfoxide to methionine has been described by Ejiri et al., Anal. Biochem. 102. 393 (1980). Briefly, the assay involved the acylation of tRNA$^{Met}$ with [$^{35}$S] methionine formed as a result of the enzymatic reduction of [$^{35}$S] MetSO. The assay can detect the formation of less than 1 pmol of methionine.

EXAMPLE 4

Assay for reduction of MetSO enkephalin

The reaction mixture for assaying the reduction of MetSO-enkephalin contained in a total volume of 15 µl: 33 mM Tris-Cl, pH 7.4, 13 mM $MgCl_2$, 13 mM DTT, 204 pmol [$^3$H] MetSO-enkephalin and 3.2 µg of the peptide MetSO reductase. The reaction mixture was incubated for 60 min at 37°, placed on ice, 1 mmol of Met-enkephalin was added and the volume brought to 0.5 ml with $H_2O$. An aliquot was applied to an RP-8 HPLC column and the column eluted with a gradient from 0 to 20% n-propanol, as described by Lewis et al supra in Example 1. Fractions were collected and assayed for radioactivity. two peaks of radioactivity were observed corresponding to Met-enkephalin and MetSO-enkephalin. The amount of radioactivity which eluted with the Met-enkephalin was used to calculate the extent of reduction of MetSO-enkephalin.

EXAMPLE 5

Purification of L12-transacetylase

Five hundred grams of *E. coli* Q13 was suspended in an equal volume of buffer containing 10 mM Tris-acetate, pH 7.8, 14 mM Mg acetate, 50 mM NH4Cl, and 6 mM β-mercaptoethanol and disrupted in a Manton Gaulin homogenizer. The suspension was centrifuged at 30,000×g and the supernatant solution fractionated with ammonium sulfate. The protein (15,000 mg) precipitating between 35–60% ammonium sulfate saturation was dissolved in buffer B (10 mM Tris-Cl, pH 7.5, 10 mM MgCl2, 50 mM KCl, 1 mM β-mercaptoethanol and 10% glycerol) and dialyzed overnight against buffer B. The protein solution was then chromatographed on a DE-52 column (5×50 cm) which had been equilibrated with buffer B. The protein was eluted using a 100–400 mM KCl gradient in buffer B. The enzyme activity eluted at about 230 mM KCl and these fractions were pooled (8000 mg), concentrated by pressure filtration, and aliquots were chromatographed on Sephadex G-100 columns (5×100 cm) that had been equilibrated with a buffer containing 10 mM Tris-Cl, pH 7.5, 1 mM MgCl2, 1 mM β-mercaptoethanol and 10% glycerol.

The fractions containing the enzyme activity were pooled (750 mg), concentrated and applied to a hydroxyapatite column (2×15 cm) equilibrated with a buffer containing 25 mM KPO4, pH 6.9, 1 mM β-mercaptoethanol and 10% glycerol. The column was eluted with a gradient from 25 mM to 250 mM KPO4, pH 6.9, containing 1 mM β-mercaptoethanol and 10% glycerol and the fractions containing enzymatic avtivity were pooled and concentrated (72 mg). This procedure yielded a 225 fold purification of the enzyme. Under standard conditions of assay as set forth by Brot and Weissbach [Biochem. Biophys. Res. Commun. 49, 673 (1972)] this fraction acetylated 46 nmols of Met-L12 per mg protein in 5 min. The conversion of Met-L12 to acytyl-Met-L12 catalyzed by this enzyme is linear with Met-L12 concentration and MetSO-L12 is not a substrate for this enzyme. These properties are essential in order to use the enzymatic acetylation of Met-L12 as an assay for MetSO-L12 reduction. It was seen that at all concentrations of Met-L12, only one-third of the protein is acetylated.

EXAMPLE 6

Purification of Peptide MetSO-reductase

Two hundred grams of *E.coli* $Z^{19}$ cells, grown in L-broth to mid-log phase were harvested, suspended in 300 ml of a buffer containing 10 mM each of Tris-HCl, pH 7.4, MgCL2, NH4Cl and 1 mM β-mercaptoethanol (buffer C) and disrupted by sonication. The suspension was centrifuged at 30,000×g and the supernatant was brought to 80% saturation with (NH4)2SO4. The precipitate was centrifuged and suspended in a buffer containing 20 mM Tris, pH 7.4, 25 mM KCl, 2 mM β-mercaptoethanol and 15% glycerol (buffer D) and dialyzed against this buffer. This material (4,500 mg) was applied onto a DE-52 column (5×25 cm) which had been equilibrated with buffer D and the column was eluted with a gradient from 25 mM to 500 mM KCl in buffer D. The fractions containing the enzymatic activity were pooled (the enzyme eluted at about 230 mM KCl) brought to 80% saturation with (NH4)2SO4 and the precipitate (1938 mg) dissolved in buffer C and chromatographed on an Ultrogel AcA-44 column (2.5×100 cm) equilibrated with buffer C. The column was eluted with buffer C and the fractions containing enzymatic activity were pooled and concentrated by pressure dialysis.

This material (151 mg) was then loaded onto a DEAE-Sephadex column equilibrated with buffer D and the column eluted with a gradient from 25 mM KCl to 500 mM KCl in buffer D. The active fractions were pooled and concentrated by pressure filtration (36 mg). Using the two-step assay described above, 1 μg of the purified protein catalyzed the reduction of an amount of MetSO-L12 so that between 14–19 pmol of acetyl-Met-L12 were formed in the acetylation reaction using L12 transacetylase. It was estimated that the resulting partially purified peptide MetSO reductase was purified about 20-fold by this procedure. An exact value could not be obtained since there was not a linear relationship at low protein levels between protein concentration and reductase activity, especially with the less pure fractions. The partially purified peptide MetSO reductase preparation did not contain any L12 transacetylase activity.

EXAMPLE 7

Preparation of tissue and cell extracts

Three month old male rats (150 gm) were killed by cervical dislocation and the various organs rapidly removed and placed on ice. Each organ was suspended in an equal volume (g/ml) of buffer B and homogenized in a Tekmar tissue homogenizer. *Euglena gracilis* was grown in the dark at 27° in a heterotrophic medium as described by Fox et al., J. Biol. Chem. 255, 6018 (1980). After the cells had reached a density of $0.8 \times 10^5$ cells/ml they were exposed to about 400 foot candles of fluorescent light. After 48 hrs of exposure to light the cells were harvested, suspended in buffer B, and sonicated. *Tetrahymena pyriformis* was grown at 30° as described by Campbell and Weissbach, J. Biol. Chem. 255, 4691 (1980) and harvested at $1.2 \times 10^5$ cells/ml. The cells were suspended in buffer B and disrupted by sonication. HeLa S-3 cells were grown at 37° to a density of $1 \times 10^8$ cells/ml in F-13 medium (Gibco), harvested, suspended in an equal volume of buffer B and disrupted by sonication. Spinach was obtained from a local purveyor and the leaves dissected free of the stalks. The leaves were homogenized in 3 volumes of buffer B in a Waring blender.

An S-30 extract was prepared from all of the above broken cell extracts by centrifugation at 30,000×g for 20 min. The supernatant fraction was used as the source of the enzyme and incubations were for 60 min as described in Example 6 for the assay of the *E. coli* peptide MetSO reductase.

EXAMPLE 8

Reduction of MetSO-L12

It was noted previously that purified preparations of the *E. coli* enzyme described by Ejiri et al. that catalyzed the reduction of free MetSO to Met did not reduce MetSO-L12 to L12. Since crude *E. coli* extracts had the latter activity, attempts were made to purify this protein(s). The assay was based on the ability of L12 to be enzymatically acetylated as compared to MetSO-L12. A partially purified preparation that catalyzed the reduction of MetSO-L12 to L12 was obtained by ammo- nium sulfate fractionation and chromatography on DEAE-cellulose, Ultrogel AcA-44 and DEAE-Sephadex. With the purified enzyme preparation, the reaction was proportional to protein concentrations above 1 μg per reaction mixture and was linear for 60 min of incubation.

Table 1 shows that the reaction is dependent on peptide MetSO-reductase, MetSO-L12 and DTT. Optimum amounts of DTT were used and the DTT cannot be replaced by β-mercaptoethanol. It can also be seen that the dithiol appears to be substituting for the normal reductant, i.e. thioredoxin. Thus when the DTT is replaced by reduced triphosphopyridine nucleotide (TPNH), thioredoxin and thioredoxin reductase there is a large stimulation in the amount of acetyl-L12 formed.

TABLE I

Requirements for the Reduction of MetSO-L12

| System | Acetyl-L12 formed pmoles |
|---|---|
| Complete | 16.6 |
| -Enzyme | 1.3 |
| -MetSO-L12 | 0 |
| -DTT | 3.7 |
| -DTT + β-Mercaptoethanol | 1.0 |
| -DTT, + TPNH, + Thioredoxin, + Thioredoxin reductase | 52.7 |

The assay and incubation conditions are described in the text. Where indicated, the incubations contained one μg of peptide MetSO-reductase, 1.4 μg thioredoxin, 3 μg thioredoxin reductase and 50 nmole TPNH.

As mentioned above, the highly purified enzyme that catalyzed the reduction of free MetSO to methionine could not catalyze the reduction of MetSO-12. In a similar manner, the partially purified fraction that catalyzed the reduction of MetSO-L12 had little activity against free MetSO. The molecular weight of the peptide MetSO reductase was estimated to be between 18,000–20,000 from its elution profile from the Ultrogel column. In addition, the reduction of MetSO-L12 to Met-L12 was not significantly inhibited by a large excess of MetSO. At $1 \times 10^{-4}$ M MetSO (about 60 times the concentration of MetSO-L12 used) there was less than 20% inhibition.

MetSO-enkephalin, which has the sequence Tyr-Gly-Gly-Phe-MetSO, is also a substrate for the enzyme and in the presence of DTT, the oxidized pentapeptide is reduced to Met-enkephalin. Although this reaction is stimulated by DTT, the reason for the lack of a more complete dependency is not clear.

TABLE II

Reduction of MetSO-Enkephalin by E. coli peptide MetSO Reductase

| Omission | Met-Enkephalin pmoles |
|---|---|
| Complete | 32 |
| -Enzyme | 2 |
| -DTT | 15 |

EXAMPLE 9

Preliminary studies on distribution of the enzyme

The activity that reduces MetSO-L12 to L12 also has been detected in a variety of cells. Cell free S-30 extracts were prepared from Euglena gracilis, Tetrahymena pyriformis, spinach, HeLa cells, and various rat tissues as described in Example 7. Table III summarizes the reductase activity in the different extracts. In all cases, significant reduction of MetSO-L12 was evident. However, because of the possible presence of activators or inhibitors in the extracts, and the inability to obtain a linear relationship between activity and amount of extract, the values in Table III should be used only for qualitative comparison.

TABLE III

Activity of peptide MetSO Reductase in Crude Extracts

| Source | Acetyl-Met-L12 formed pmoles |
|---|---|
| E. coli | 850 |
| Euglena gracilis | 2600 |
| Tetrahymena pyriformis | 150 |
| Spinach | 650 |
| HeLa | 330 |
| Liver (rat) | 960 |
| Kidney (rat) | 923 |
| Heart (rat) | 710 |
| Lung (rat) | 359 |
| Brain (rat) | 181 |

The values represent pmoles of acetyl-Met-L12 formed per mg protein under the incubation and assay conditions.

What is claimed is:

1. Peptide MetSO reductase being an enzyme endogenous to biological cells and being essentially free of other endogenous peptides, said reductase being characterized as follows:
   (i) having the ability to reduce methionine sulfoxide residues in peptides to methionine;
   (ii) unable to reduce free methionine sulfoxide to methionine;
   (iii) having a molecular weight of about 18,000 to 20,000 (Ultragel); and
   (iv) being free of transacetylase activity.

2. A method for reducing methionine sulfoxide groups in peptides containing such groups which method comprises reacting such peptide with the reductase of claim 1.

3. The method of claim 2 wherein said reaction is carried out in the presence of dithiothreitol.

4. The method of claim 2 wherein said reaction is carried out in the presence of dithiothreitol, reduced triphosphopyridine nucleotide, thioredoxin and thioredoxin reductase.

5. The method of claim 2 wherein said peptide is MetSO-L12.

6. The method of claim 2 wherein said peptide is MetSO-enkephalin.

7. The method of claim 2 wherein said peptide is inactivated alpha-1-proteinase inhibitor.

* * * * *